(12) United States Patent
Yun et al.

(10) Patent No.: US 11,083,561 B2
(45) Date of Patent: Aug. 10, 2021

(54) DEVICE FOR COATING INSIDE OF ARTIFICIAL BLOOD VESSEL

(71) Applicant: MEDIPHARMAPLAN CO., LTD., Eumseong-gun (KR)

(72) Inventors: Eung Jun Yun, Guri-si (KR); Ju Won Jeong, Jincheon-gun (KR); Tae Sup Byun, Seoul (KR); Dae Joong Kim, Seongnam-si (KR); Insu Baek, Anyang-si (KR); Chengzhe Bai, Hwaseong-si (KR)

(73) Assignee: NSJ MEDICAL CO., LTD., Seoul (KR)

( * ) Notice: Subject to any disclaimer, the term of this patent is extended or adjusted under 35 U.S.C. 154(b) by 0 days.

(21) Appl. No.: 16/072,526

(22) PCT Filed: Nov. 11, 2016

(86) PCT No.: PCT/KR2016/013039
§ 371 (c)(1),
(2) Date: Jul. 25, 2018

(87) PCT Pub. No.: WO2018/070591
PCT Pub. Date: Apr. 19, 2018

(65) Prior Publication Data
US 2019/0314135 A1    Oct. 17, 2019

(30) Foreign Application Priority Data
Oct. 10, 2016  (KR) .................. 10-2016-0130610

(51) Int. Cl.
*B05B 13/06*    (2006.01)
*B05C 9/12*    (2006.01)
(Continued)

(52) U.S. Cl.
CPC .............. *A61F 2/062* (2013.01); *A61L 27/34* (2013.01); *A61L 27/54* (2013.01); *B05B 13/02* (2013.01);
(Continued)

(58) Field of Classification Search
CPC ................................ B05B 13/06; B05C 13/02
See application file for complete search history.

(56) References Cited

U.S. PATENT DOCUMENTS 2,285,370 A * 6/1942 Staelin .................... B29C 41/08
264/82
4,197,000 A * 4/1980 Blackwood ......... B05B 13/0228
396/625

(Continued)

FOREIGN PATENT DOCUMENTS

JP    2010-137041    6/2010
KR    10-0932688    12/2009
(Continued)

*Primary Examiner* — Binu Thomas
(74) *Attorney, Agent, or Firm* — Lex IP Meister, PLLC

(57) ABSTRACT

The present invention relates to a device for coating the inside of an artificial blood vessel and, to explain more specifically, to a device for coating the inside of an artificial blood vessel inserted into the body of a human for a medical purpose, which is configured to be able to selectively coat just the inside of a lumen of the artificial blood vessel with a bioactive substance for inhibiting neointimal hyperplasia, (Continued)

in order to prevent a side effect, such as angiostenosis or inflammation, from occurring in an area connecting the artificial blood vessel and a blood vessel in the body.

7 Claims, 4 Drawing Sheets

(51) Int. Cl.
*B05B 13/02* (2006.01)
*B05C 13/02* (2006.01)
*A61F 2/06* (2013.01)
*A61L 27/34* (2006.01)
*A61L 27/54* (2006.01)
*B05C 7/02* (2006.01)
*A61L 27/58* (2006.01)

(52) U.S. Cl.
CPC ...... *B05B 13/0627* (2013.01); *B05B 13/0654* (2013.01); *B05C 7/02* (2013.01); *B05C 9/12* (2013.01); *B05C 13/02* (2013.01); *A61F 2210/0076* (2013.01); *A61L 27/58* (2013.01); *A61L 2300/41* (2013.01); *A61L 2300/416* (2013.01); *B05B 13/0609* (2013.01); *B05B 13/0618* (2013.01)

(56) References Cited

U.S. PATENT DOCUMENTS

| | | | |
|---|---|---|---|
| 5,038,708 A * | 8/1991 | Wells | B05B 13/0627 118/313 |
| 2004/0062860 A1* | 4/2004 | Nakashima | F16C 33/201 427/233 |
| 2005/0209687 A1 | 9/2005 | Sitzmann et al. | |
| 2007/0028429 A1* | 2/2007 | Ishida | A45C 13/1069 24/303 |
| 2008/0121175 A1* | 5/2008 | Pacetti | B05B 7/061 118/600 |
| 2011/0088617 A1* | 4/2011 | Bottger | B05B 13/06 118/317 |

FOREIGN PATENT DOCUMENTS

| | | |
|---|---|---|
| KR | 10-2010-0084059 | 7/2010 |
| KR | 10-1417749 | 7/2014 |

* cited by examiner

[Fig. 1]
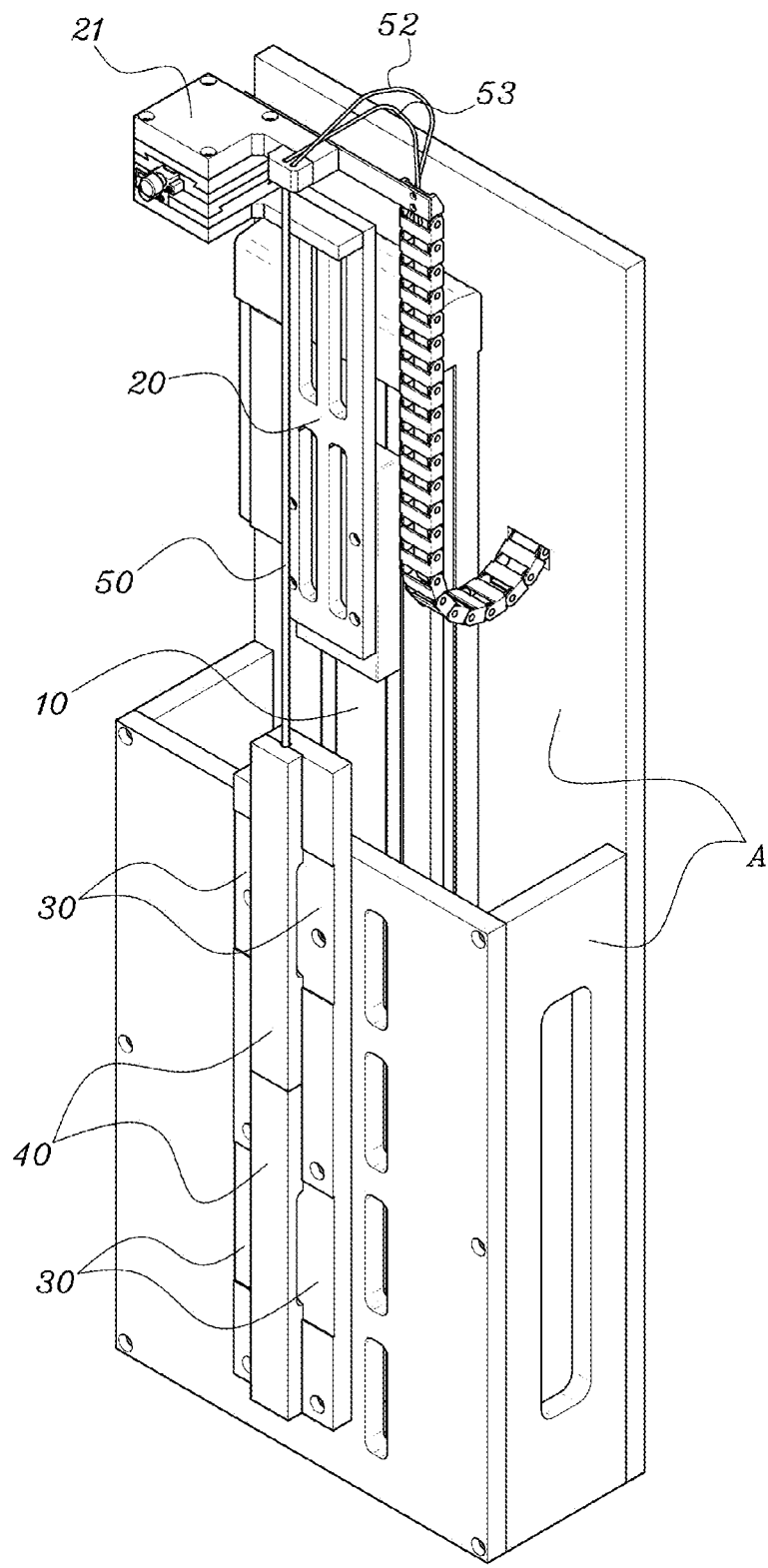

[Fig. 2]
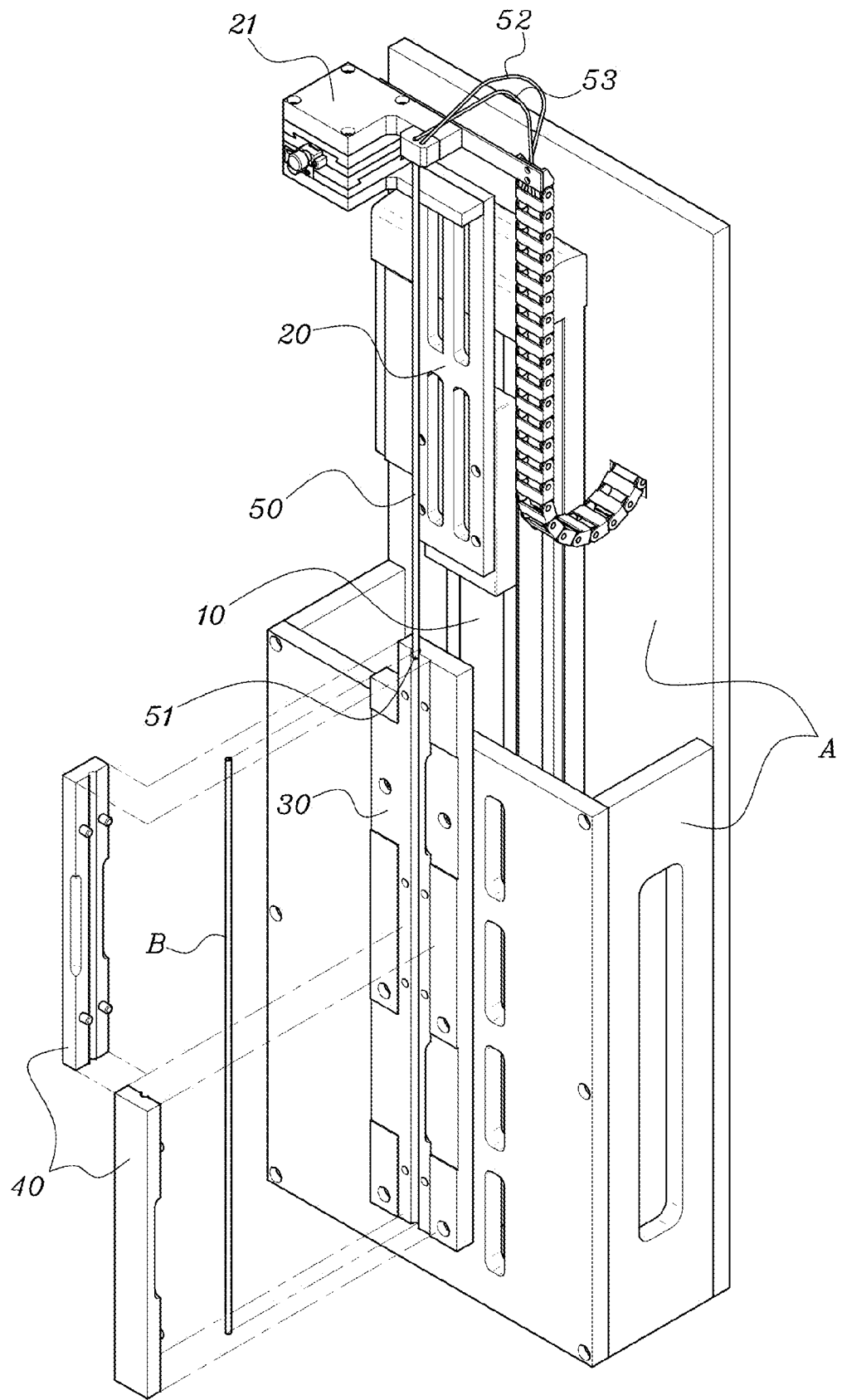

[Fig. 3]
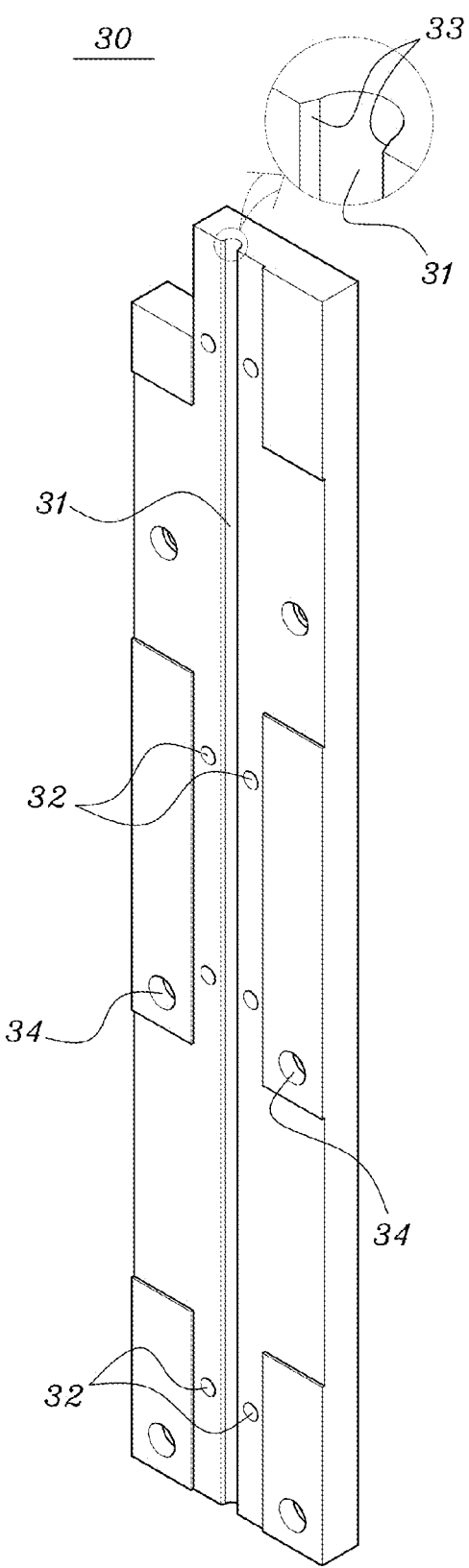

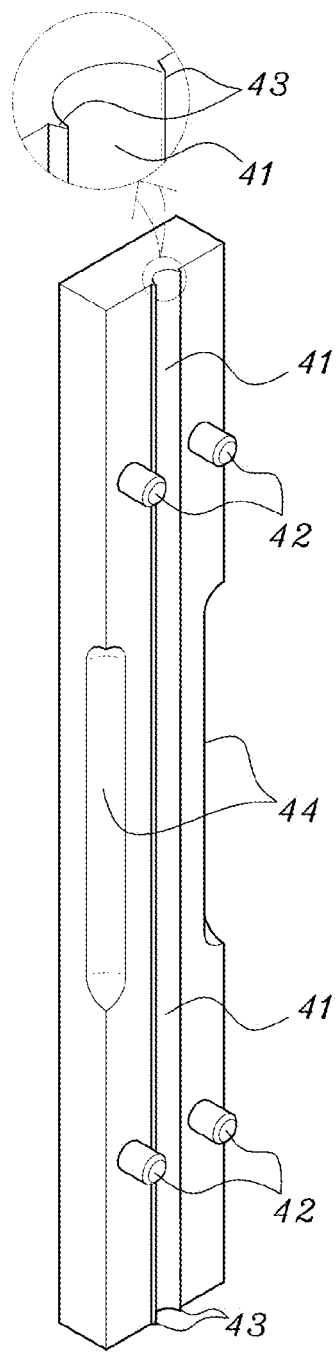
[Fig. 4]

DEVICE FOR COATING INSIDE OF ARTIFICIAL BLOOD VESSEL

TECHNICAL FIELD

The present invention relates to a device for coating the inside of an artificial blood vessel and, more specifically, to a device for coating the inside of an artificial blood vessel inserted into the body of a human for a medical purpose, which is configured to be able to selectively coat just the inside of a lumen of the artificial blood vessel with a bioactive substance for inhibiting neointimal hyperplasia, in order to prevent a side effect, such as angiostenosis or inflammation, from occurring in an area connecting the artificial blood vessel and a blood vessel in the body.

BACKGROUND ART

In case where a cylindrical structure having a lumen like an artificial blood vessel is inserted into the body of a human, generally, angiostenosis may occur at a connected portion to a blood vessel in the body or inflammation may occur at a contacted portion with surrounding tissues of the artificial blood vessel. So as to suppress such side effects, a technology has been proposed to coat a bioactive substance inhibiting neointimal hyperplasia onto a surface of the artificial blood vessel.

The artificial blood vessel coated with the bioactive substance like paclitaxel or rapamycin desirably provides a remarkably more reduced occurrence rate in angiostenosis or inflammation when compared with a control group. However, unfortunately, the bioactive substance suppresses myofibroblasts on the surrounding tissues of the artificial blood vessel from being expanded. If the myofibroblasts are not sufficiently expanded, the surrounding tissues of the body cannot rigidly support the artificial blood vessel.

For example, an artificial blood vessel is implanted to allow a chronic renal failure patient to receive hemodialysis, and in this case, if myofibroblasts on the surrounding tissues of the artificial blood vessel are not sufficiently expanded, the artificial blood vessel is not rigidly fixed to the surrounding tissues, so that after the hemodialysis, bleeding occurs around the artificial blood vessel. So as to avoid such side effects, accordingly, many endeavors have been made in conventional practices.

To solve the above-mentioned problems, for example, a coating method is disclosed in Korean Patent No. 10-1034654 (Dated on May 4, 2011), wherein so as to allow at least one of an inner peripheral surface and an outer peripheral surface of a structure having a lumen to be coated with bioactive substances with different densities, a coating liquid made by dissolving the bioactive substances in a mixture solvent obtained by mixing two or more solvents having different characteristics flows to the inside of the structure.

For another example, an implantation tube and a method for coating the same is disclosed in Korean Patent No. 10-1119011 (Dated on Feb. 15, 2012), wherein an inner peripheral surface of a structure having a lumen is coated with a substance for inhibiting neointimal hyperplasia, and an outer peripheral surface thereof is coated with a bioactive substance for accelerating the expansion of myofibroblasts.

Further, a cylindrical structure having a lumen and adapted to be inserted into the body of a human is disclosed in Korean Patent No. 10-1240437 (Dated on Feb. 28, 2013), wherein a coated layer is formed on portions of one or more inner peripheral surfaces of both side ends of the structure, and the coated layer includes a polymer for controlled release and a bioactive substance.

As mentioned above, the conventional methods for coating the inside of the artificial blood vessel with the bioactive substance are carried out by delivering the coating liquid containing the bioactive substance to the inside of the lumen of the artificial blood vessel, but through the conventional coating liquid delivery methods, it is very hard to form a uniformly coated film in the inside of the artificial blood vessel.

So as to solve the above-mentioned problems, accordingly, an artificial blood vessel coating system is disclosed in Korean Patent No. 10-1417749 (Dated on Jul. 3, 2014), wherein an injection hole of an injection nozzle is inserted into the inside of an artificial blood vessel to inject a coating substance, while moving from one end of the artificial blood vessel to the other end thereof, and at the same time to apply a pneumatic pressure to the artificial blood vessel, so that the coating substance is radially injected from the end of the injection hole through a spiral passage of the injection hole and is uniformly coated over the inside of the artificial blood vessel.

PRIOR ART DOCUMENTS (Patent document 1) Korean Patent No. 10-1034654 (Dated on May 4, 2011)
(Patent document 2) Korean Patent No. 10-1119011 (Dated on Feb. 15, 2012)
(Patent document 3) Korean Patent No. 10-1240437 (Dated on Feb. 28, 2013)
(Patent document 4) Korean Patent No. 10-1417749 (Dated on Jul. 3, 2014)

DISCLOSURE

Technical Problem

By the way, the prior art, Korean Patent No. 10-1417749 relates to the injection nozzle for coating the artificial blood vessel, but a detailed explanation on a structure or operating method of a coating device to which the injection nozzle is adopted is not given therein. Typically, the artificial blood vessel has just a diameter of 5 to 6 mm and a length of 40 cm and is made of a substantially soft material, and accordingly, it is impossible that the inside of the artificial blood vessel is uniformly coated through the conventional coating devices.

Accordingly, the present invention has been made in view of the above-mentioned problems occurring in the prior art, and it is an object of the present invention to provide a device for coating the inside of an artificial blood vessel that is adapted to uniformly coat just the inside of a lumen of the artificial blood vessel with a bioactive substance.

Technical Solution

To accomplish the above-mentioned object, according to the present invention, there is provided a device for coating the inside of an artificial blood vessel, which includes: a guide rail fixedly disposed on a frame in upward and downward directions thereof; a lifting member reciprocatedly moved along the guide rail in the upward and downward directions; an artificial blood vessel support board disposed on the lower end portion of the frame and having a first semicircular groove formed linearly on the front surface thereof along a moving direction of the lifting member, the first semicircular groove having the same radius as the artificial blood vessel; an artificial blood vessel cover board detachably mounted on the artificial blood vessel support board and having a second semicircular groove formed on a corresponding position to the first semicircular groove, the second semicircular groove having the same radius as the artificial blood vessel; and a coating liquid injection tube disposed elongatedly in the upward and downward directions on the lifting member and having a nozzle tip located on a lower end periphery thereof, so that if the lifting member is ascended and descended, the coating liquid injection tube is inserted or drawn into/from the artificial blood vessel supported between the first semicircular groove and the second semicircular groove to allow a coating liquid and gas to be injected through the nozzle tip.

Advantageous Effects

According to the present invention, the device for coating the inside of the artificial blood vessel is configured to be able to uniformly coat just the inside of the lumen of the artificial blood vessel with the bioactive substance for inhibiting neointimal hyperplasia and to completely prevent the outside of the artificial blood vessel from coming into contact with the bioactive substance, so that the artificial blood vessel can be excellently attached to the surrounding tissues thereof after implanted in the body of a human.

DESCRIPTION OF DRAWINGS

FIG. 1 is a perspective view showing a device for coating the inside of an artificial blood vessel according to the present invention.

FIG. 2 is a separate perspective view showing main parts of FIG. 1.

FIG. 3 is a perspective view showing an artificial blood vessel support board of FIG. 1.

FIG. 4 is a perspective view showing an artificial blood vessel cover board of FIG. 1.

EXPLANATION ON REFERENCE NUMERALS IN THE DRAWINGS

| 10: guide rail | 11: lifting member |
| 21: controller board | 30: artificial blood vessel support |
| 31, 41: semicircular groove | 32: guide hole |
| 33: boundary groove | 34: screw hole |
| 40: artificial blood vessel cover board | |
| 42: guide protrusion | |
| 43: boundary projection | 44: handle groove |
| 50: coating liquid injection tube | 51: nozzle tip |
| 52: coating liquid supply line | 53: gas supply line |
| A: frame | B: artificial blood vessel |

BEST MODE FOR INVENTION

Hereinafter, the present invention will now be described in detail with reference to the attached drawings. Before the present invention is disclosed and described, it is to be understood that the disclosed embodiments are merely exemplary of the invention, which can be embodied in various forms. If it is determined that the detailed explanation on the well known technology related to the present invention makes the scope of the present invention not clear, the explanation will be avoided for the brevity of the description.

For the convenience of the description, around FIG. 1, the side at which a lifting member 20 is located is called 'upper side' or 'upward side', and the side at which an artificial blood vessel support board 30 is located is called 'lower side' or 'downward side'.

As shown in FIGS. 1 and 2, a device for coating the inside of an artificial blood vessel according to the present invention includes a guide rail 10, a lifting member 20, an artificial blood vessel support board 30, an artificial blood vessel cover board 40, and a coating liquid injection tube 50.

First, the guide rail 10 is fixedly disposed on a frame A of the device according to the present invention in upward and downward directions. Further, the lifting member 20 is reciprocatedly moved along the guide rail 10 by a given distance in upward and downward directions.

Structures and operating ways of the guide rail 10 and the lifting member 20 are carried out in various manners through known technologies, within a technical scope of the present invention. However, the lifting member 20 is controlled to be ascended and descended by the same distance as a length of an object to be coated, that is, an artificial blood vessel B.

Next, the artificial blood vessel support board 30 is fixedly disposed on the lower end portion of the frame A, and as shown in FIG. 3, the artificial blood vessel support board 30 includes a first semicircular groove 31 formed linearly on the front surface thereof along a moving direction of the lifting member 20. The first semicircular groove 31 has a sectional shape of a semicircle and has the same radius as the artificial blood vessel B. Accordingly, the first semicircular groove 31 has a given size and depth so that it can accommodate half of the artificial blood vessel B in a diameter direction of the artificial blood vessel B therein. Further, a length of the first semicircular groove 31 is the same as the artificial blood vessel B.

The artificial blood vessel cover board 40 is detachably mounted on the artificial blood vessel support board 30, and as shown in FIG. 4, the artificial blood vessel cover board 40 has a second semicircular groove 41 formed on one surface thereof in such a manner as to correspond to the first semicircular groove 31. A size, depth, and length of the second semicircular groove 41 are the same as the first semicircular groove 31. The first semicircular groove 31 and the second semicircular groove 41 are coupled to each other to form a circular artificial blood vessel insertion hole having the same inner diameter as the outer diameter of the artificial blood vessel B.

Accordingly, the artificial blood vessel B is inserted into the first semicircular groove 31 of the artificial blood vessel support board 30, and next, if the artificial blood vessel B is covered with the artificial blood vessel cover board 40, it can be rigidly supported in a state of being straightly disposed in the artificial blood vessel insertion hole. The artificial blood vessel cover board 40 is divided into two pieces separated from each other in upward and downward directions thereof in such a manner as to be easily manipulated.

Lastly, as shown in FIGS. 1 and 2, the coating liquid injection tube 50 is disposed elongatedly in upward and downward directions on the lifting member 20 and has a nozzle tip 51 located on a lower end periphery thereof to inject nitrogen or argon gas, together a coating liquid, into the artificial blood vessel B. A length of the coating liquid injection tube 50 is a little greater than that of the coating liquid injection tube 50, and desirably, the length is 42 to 45 cm. If the lifting member 20 is descended in the state where the artificial blood vessel B is supportedly located in the artificial blood vessel insertion hole, the nozzle tip 51 is inserted into a bottom of the artificial blood vessel B.

The coating liquid injection tube 50 has a coating liquid supply line 52 connected to a top end periphery thereof to supply the coating liquid to the nozzle tip 51 and a gas supply line 53 connected to the top end periphery thereof to supply the nitrogen or argon gas, and the lifting member 20 has a controller 21 located on one side thereof to control the coating liquid supply line 52 and the gas supply line 53. The nitrogen or argon gas injected together with the coating liquid serves to atomize the coating liquid and thus to form a uniform coated film.

According to the present invention, as shown in FIGS. 3 and 4, the artificial blood vessel cover board 40 has guide protrusions 42 for alignment protruding therefrom, and the artificial blood vessel support board 30 has guide holes 32 adapted to insert the guide protrusions 42 thereinto. The guide holes 32 have magnets (not shown) located at interiors thereof to pull the guide protrusions 42. The guide holes 32 and the guide protrusions 42 serve to allow the artificial blood vessel support board 30 and the artificial blood vessel cover board 40 to be aligned so that they always come into close contact with each other at a constant position.

According to the present invention, the artificial blood vessel support board 30 has a hinge (not shown) disposed on one side thereof to rotatably support one side of the artificial blood vessel cover board 40. In detail, the artificial blood vessel cover board 40 can rotate like a hinged door, so that the first semicircular groove 31 and the second semicircular groove 41 are open and closed, thereby making it easy to manipulate them.

Further, the second semicircular groove 41 has boundary projections 43 protruding from both sides thereof in a longitudinal direction thereof, and the first semicircular groove 31 has boundary grooves 33 formed on both sides thereof in a longitudinal direction thereof to accommodate the boundary projections 43 therein. The boundary grooves 33 and the boundary projections 43 serve to allow the first semicircular groove 31 and the second semicircular groove 41 to form the artificial blood vessel insertion hole to a shape of a complete circle when the artificial blood vessel support board 30 is covered with the artificial blood vessel cover board 40.

A reference numeral 34 not explained in FIG. 3 indicates a screw hole into which a coupling screw for fixing the artificial blood vessel support board 30 to the frame A is inserted, and a reference numeral 44 not explained in FIG. 4 indicates a handle groove for easily holding the artificial blood vessel cover board 40.

Through the control of the controller 21 of the lifting member 20, on the other hand, the coating liquid is injected into the artificial blood vessel B only when the coating liquid injection tube 50 is ascended after descended to the artificial blood vessel B. While the nozzle tip 51 is moving, as a result, it does not give any damage to the coated film on the inner periphery of the artificial blood vessel B.

At this time, desirably, the nozzle tip 51 is ascended at a speed of 300 to 600 mm/min. If the ascending speed of the nozzle tip 51 is over the above-mentioned range, the coated film is not uniform, or the coating liquid is excessively injected to overflow to the outside of the artificial blood vessel B.

If the coating liquid injection tube 50 is ascended, while injecting the coating liquid and the gas, to allow the nozzle tip 51 to reach a top dead point, the nozzle tip 51 stops injecting the coating liquid and injects only the nitrogen or argon gas into the artificial blood vessel B for about two minutes to dry the coated film.

According to the present invention, the coating liquid is a mixture solution comprising a bioactive substance, a polymeric substance, and a volatile solvent. The bioactive substance serves to suppress occurrence of angiostenosis or inflammation, and examples of the bioactive substance include paclitaxel, methotrexate, rapamycin, tacrolimus, cyclosporine A, dexamethasone, dexamethasone phosphate, dexamethasone acetate, and so on.

Further, the polymeric substance serve to control an amount of the bioactive substance discharged, and examples of the polymeric substance include a single compound of protein polymer like collagen, cellulose polysaccharide like cellulose acetate, polysaccharide like hyaluronic acid, polyester like poly lactic acid, polyglycolic acid, etc., polyanhydride, or polycaprolactone, copolymers thereof, and compounds thereof.

The solvent serves to allow the coating liquid to be uniformly coated onto the inside of the artificial blood vessel, and an example of the solvent includes acetone, methylene chloride, or a mixture thereof.

Further, the artificial blood vessel is made of e-PTFE (expanded poly tetrafluoro ethylene), polyethylene terephthalate, polyurethane, polyester, olefin polymer, or the like. Among them, the e-PTFE is a thin film having fine pores, which is elongated through high temperature and high pressure extrusion and has a substantially low coefficient of friction, so that when the e-PTFE comes into contact with blood, it delays the absorption of protein into the blood, thereby providing excellent anti-thrombotic performance.

The artificial blood vessel B with the lumen whose inside is coated with the bioactive substance using the device according to the present invention is used as a hemodialysis catheter tube connected to an artery or vein, a substitution blood vessel for a disease like critical limb ischemia or CABG (coronary artery bypass graft), or an artificial lymphatic vessel for connecting lymphatic vessels.

The invention claimed is:

1. A device for coating the inside of an artificial blood vessel, the device comprising:
   a guide rail fixedly disposed on a frame in upward and downward directions thereof;
   a lifting member reciprocatedly moved along the guide rail in the upward and downward directions;
   an artificial blood vessel support board fixed on the lower end portion of the frame and having a first semicircular groove formed linearly on the front surface thereof along a moving direction of the lifting member, the first semicircular groove having the same radius as the artificial blood vessel and having a first open bottom end and a first open top end;
   an artificial blood vessel cover board detachably mounted on the artificial blood vessel support board and having a second semicircular groove formed on a corresponding position to the first semicircular groove to support the artificial blood vessel in a straightened state, the second semicircular groove having the same radius as the artificial blood vessel and having a second open bottom end and a second open top end respectively disposed to correspond to the first open bottom end and the first open top end;
   a coating liquid injection tube disposed elongatedly in the upward and downward directions on the lifting member and having a nozzle tip located on a lower end periphery thereof, so that the coating liquid injection tube is inserted into the artificial blood vessel up to the first open bottom end and the second open bottom end or drawn from the artificial blood vessel supported between the first semicircular groove and the second semicircular groove in accordance with ascending and descending of the lifting member to allow a coating liquid and gas to be injected through the nozzle tip;

a coating liquid supply line supplying the coating liquid to the coating liquid injection tube;

a gas supply line supplying the gas to the coating liquid injection tube; and a controller controlling the coating liquid supply line and the gas supply line, wherein the first semicircular groove and the second semicircular groove extend in a straight line from the first and second open top ends to the first and second open bottom ends for straightening and supporting the artificial blood vessel.

2. The device according to claim 1, wherein the artificial blood vessel cover board is divided into two pieces separated from each other in upward and downward directions thereof.

3. The device according to claim 1, wherein the artificial blood vessel cover board has guide protrusions for alignment protruding therefrom, and the artificial blood vessel support board has guide holes adapted to insert the guide protrusions thereinto, the guide holes having magnets located at interiors thereof to pull the guide protrusions.

4. The device according to claim 1, wherein the artificial blood vessel support board has a hinge disposed on one side thereof to rotatably support one side of the artificial blood vessel cover board.

5. The device according to claim 1, wherein the second semicircular groove has boundary projections protruding from both sides thereof in a longitudinal direction thereof, and the first semicircular groove has boundary grooves formed on both sides thereof in a longitudinal direction thereof to accommodate the boundary projections therein.

6. The device according to claim 1, wherein the nozzle tip injects the coating liquid into the artificial blood vessel while the coating liquid injection tube is ascended, and after the coating liquid injection tube has been ascended, the nozzle tip injects nitrogen or argon gas for drying the coating liquid onto the artificial blood vessel.

7. The device according to claim 6, wherein the coating liquid injection tube is ascended at a speed of 300 to 600 mm/min.

* * * * *